United States Patent [19]

Hoffman

[11] 4,322,563

[45] Mar. 30, 1982

[54] SUBSTITUTED BIPHENYL-2-CARBOXALDEHYDES

[75] Inventor: William F. Hoffman, Lansdale, Pa.

[73] Assignee: Merck & Co., Inc., Rahway, N.J.

[21] Appl. No.: 233,522

[22] Filed: Feb. 11, 1981

Related U.S. Application Data

[63] Continuation-in-part of Ser. No. 140,321, Apr. 16, 1980, abandoned.

[51] Int. Cl.$^3$ .......................................... C07C 47/546
[52] U.S. Cl. .................................... 568/425; 568/436; 568/442; 568/433; 260/343.5; 260/429 C; 424/283; 560/53; 560/59; 562/469
[58] Field of Search ........................ 568/425; 568/436

[56] References Cited

U.S. PATENT DOCUMENTS

| | | | |
|---|---|---|---|
| 3,983,140 | 9/1976 | Endo et al. | 424/279 X |
| 4,049,495 | 9/1977 | Endo et al. | 195/36 R |
| 4,137,322 | 1/1979 | Endo et al. | 424/273 R |

FOREIGN PATENT DOCUMENTS 867421 11/1978 Belgium .

OTHER PUBLICATIONS

Endo, The Journal of Antibiotics, vol. XXXII, (1979), 852–854.
Brown et al., Jour. of the Chemical Soc., Perkin I, (1976), 1165–1169.
Murahashi et al., Jour. of Org. Chem., vol. 43, (1978), 4099–4106.

*Primary Examiner*—Bernard Helfin
*Attorney, Agent, or Firm*—William H. Nicholson; Mario A. Monaco

[57] ABSTRACT

Substituted biphenyl-2-carboxaldehydes are prepared in good yield by reacting palladium complexes of substituted benzaldehyde aniline Schiff bases with substituted phenylmagnesium bromides in the presence of at least six, preferably eight, molar equivalents of triphenylphosphine.

1 Claim, No Drawings

SUBSTITUTED BIPHENYL-2-CARBOXALDEHYDES

SUMMARY OF THE INVENTION

This is a continuation-in-part of copending application Ser. No. 140,321, filed Apr. 14, 1980 and now abandoned.

This invention relates to a small group of substituted biphenyl-2-carboxaldehydes and to a process for preparing certain difficult-to-obtain substituted biphenyl-2-carboxaldehydes which are needed as intermediates for synthetic, in vivo cholesterol synthesis inhibitors. More specifically it relates to a process for preparing compounds of the structure:

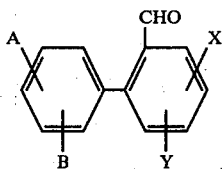

in which X, Y, A and B are each hydrogen, $C_{1-4}$ alkyl, halo (Cl, F, Br, I), $C_{1-9}$ alkoxy or benzyloxy at least one being other than hydrogen which comprises reacting a palladium complex of the structure:

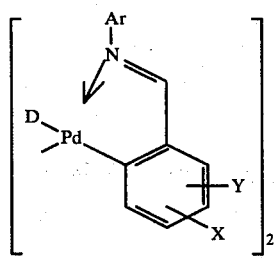

in which D is an anion such as acetate and Ar is an aromatic radical with a Grignard reagent of the structure:

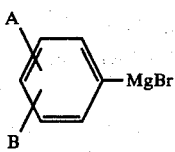

or the corresponding substituted phenyllithium in the presence of at least six, preferably eight, molar equivalents of triphenylphosphine.

BACKGROUND OF THE INVENTION

It is known that certain mevalonate derivatives inhibit the biosynthesis of cholesterol, cf. F. M. Singer et al., *Proc. Soc. Exper. Biol. Med.*, 102 270 (1959) and F. H. Hulcher, *Arch. Biochem. Biophys.*, 146 422 (1971). Nevertheless the activity of the known compounds has not always been found satisfactory, i.e. to have practical application.

Recently, Endo et al. reported (U.S. Pat. Nos. 4,049,495; 4,137,322; and 3,983,140) the production of a fermentation product which was quite active in the inhibition of cholesterol biosynthesis. This natural product, now called compactin, was reported by Brown et al. (*J. Chem. Soc.* Perkin I, 1165 (1976)) to have a complex mevalonolactone structure. However, the low rate of production from fermentation broths appears to limit the supply of this natural product.

More recently, Willard et al. (Ser. No. 67,574, filed Aug. 17, 1979) described synthetic analogs of Endo's fermentation product whose biological activity closely approximated the natural product. As the structure-activity relationship within the Willard et al. compounds was developed, the desirable structures were seen to be derived especially from 2,4-dichloro-6-substituted benzaldehydes or 2,4-dimethyl-6-substituted benzaldehydes in which the 6-substituent was a substituted phenyl. Methods of preparation of the substituted biphenyl-2-carboxaldehydes were not readily available.

Stokker (copending application Ser. No. 140,275, filed Apr. 14, 1980) devised a six-step process which made the desired aldehydes in 30–35% yield. The number of reaction steps and the low overall yield limit the usefulness of that process. Murahashi et al. (*J. Org. Chem.*, 43 4099 (1978) and Tetrahedron Letters 3749 (1974)) has described a method of preparing ortho-substituted benzaldehydes which comprises reacting a cyclic palladium complex of benzaldehyde aniline Schiff bases with a Grignard reagent in the presence of four molar equivalents of triphenylphosphine. When this reaction was tried with the substituted benzaldehydes and Grignard reagents having substituents needed for the Willard et al. inhibitors, an unusable mixture of various aldehydes was obtained.

THE PRESENT INVENTION

I have found that when the molar equivalents of triphenylphosphine are increased from the four equivalents used by Murahashi to at least six and preferably eight, the desired biphenyl-2-carboxaldehydes are obtained in 75–85% yields. The process of this invention therefore comprises preparation, in the same manner as used by Murahashi, of a palladium complex of the structure:

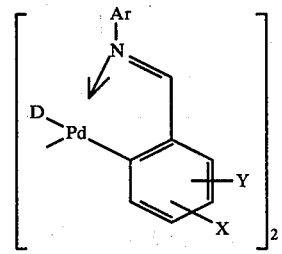

and reacting it with a Grignard reagent of structure:

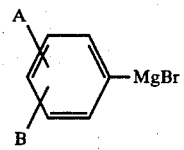

or the corresponding substituted phenyllithium in the presence of at least six and preferably eight molar equivalents of triphenylphosphine, using otherwise the procedures described by Murahashi. This synthesis is shown in Flow Sheet A. While the above formula describes a Schiff base of aniline, where Ar is phenyl, other aromatic amines having unreactive substituents such as toluidine and xylidine can obviously be used.

The aldehydes thus produced, have the structure:

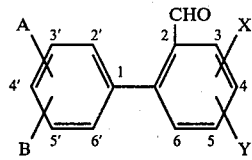

in which A, B, X and Y are each hydrogen, $C_{1-4}$ alkyl, halo such as chloro, fluoro, bromo or iodo, $C_{1-9}$ alkoxy or benzyloxy, at least one of which is other than hydrogen.

It is preferred that X and Y independently be chloro or $C_{1-4}$ alkyl, preferably methyl, and further preferred that they be in the 3- and 5-positions.

It is preferred that A and B independently be hydrogen, fluoro, $C_{1-4}$ alkyl, preferably methyl, or $C_{1-9}$-alkoxy, preferably methoxy and further that they occupy two positions selected from 3', 4' and 5'.

Preferred species which form a part of this invention are 3,5-dichloro-4'-fluoro-1,1'-biphenyl-2-carboxaldehyde; 3,5-dimethyl-4'-fluoro-1,1'-biphenyl-2-carboxaldehyde; 3,3',5-trimethyl-4'-fluoro-1,1'-biphenyl-2-carboxaldehyde; and 3,3',5,5'-tetramethyl-1,1'-biphenyl-2-carboxaldehyde.

FLOW SHEET A

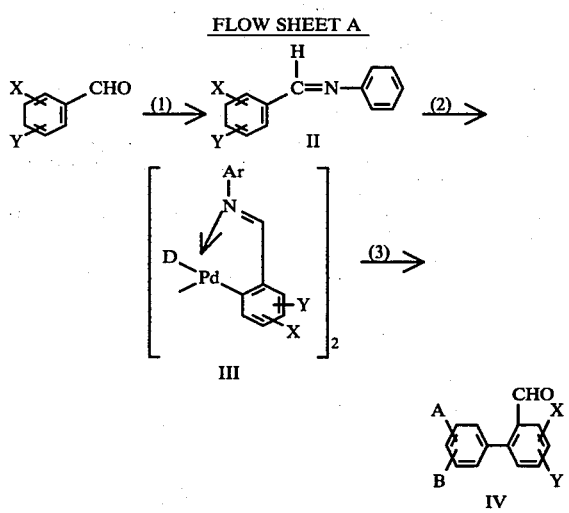

Equivalents—A, B, Y and X as defined D is an anion such as chloride or acetate.

Reactions:
(1) Reaction with aniline or other aromatic amine.
(2) Reaction with a palladium salt in the presence of an acid, e.g. palladium acetate and acetic acid.
(3) Reaction with a Grignard reagent:

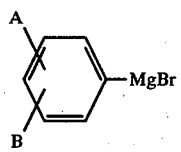

or the corresponding substituted phenyllithium in the presence of six to eight molar equivalents of triphenylphosphine in a suitable solvent such as benzene or toluene.

The biphenylaldehydes produced by the novel process of this invention are useful for the synthesis of compounds of structure X in Flow Sheet B by the process described in Flow Sheet B and the Reactions appended thereto.

The compounds, X, are potent inhibitors of HMG-CoA-reductase and hence useful as antihypercholesterolemic agents in the treatment of hypercholesterolemia in human or animal patients. A typical human adult dose is between 200 and 2,000 mg/day, which can be administered in a single dose or in divided doses given 1–4 times per day.

FLOW SHEET B

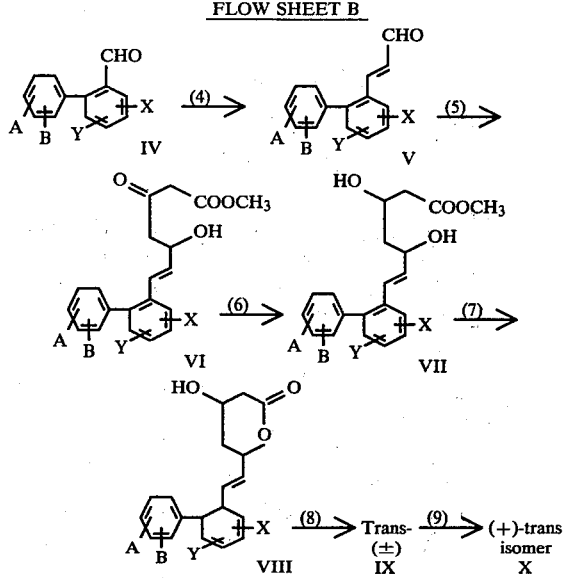

Reactions:

(4) Aldol reaction, e.g. either condensation of acetaldehyde with the benzaldehyde, followed by acetylation and thermal elimination of acetic acid, or a directed aldol condensation in which the anion of an N-substituted ethylidenylimine is condensed with the starting aldehyde, followed by dehydration and imine hydrolysis, or by reaction with 2-ethoxyvinyllithium followed by rearrangement.

(5) Reaction with the dianion of acetoacetic ester.
(6) Reduction with $NaBH_4$ at 0° C.
(7) Saponification by base, followed by lactonization in toluene.
(8) Separation of cis- and trans- isomers.
(9) Resolution.

A typical synthesis using the above reactions is described here for the preparation of (+)-(E)-trans-6-[2-(3,5-dichloro-4'-fluoro[1,1'-biphenyl]-2-yl)ethenyl]-3,4,5,6-tetrahydro-4-hydroxy-2H-pyran-2-one.

Step A: Preparation of (E)-2,4-Dichloro-6-(4-fluorophenyl)cinnamaldehyde

A 1.6 M solution (18.8 ml, 30 mmole) of n-butyllithium in hexane is added cautiously to a stirred solution of freshly distilled diisopropylamine (3.0 g, 30 mmole) in anhydrous tetrahydrofuran (200 ml) maintained at 0° C. under a nitrogen atmosphere. The resulting solution is stirred at 0° C. for 15 minutes and then treated with ethylidenecyclohexylamine (3.75 g, 30 mmole). The solution is stirred 15 minutes at 0° C., cooled to −78° C. and treated with a solution of 2,4-dichloro-6-(4-fluorophenyl)benzaldehyde (30 mmole) in anhydrous tetrahydrofuran (50 ml). The resulting solution is stirred at −78° C. for 15 minutes and then at 25° C. for 60 minutes. The reaction solution is treated with water (200 ml) and extracted with ether (3×200 ml). The organic extracts are combined, washed with brine (3×100 ml), dried over magnesium sulfate and filtered. The filtrate is evaporated in vacuo, leaving the desired intermediate hydroxyimine as a brown viscous oil.

A solution of the oily imine in tetrahydrofuran (110 ml) is treated with a solution of oxalic acid dihydrate (11 g, 87.2 mmole) in water (22 ml). The resulting solution is refluxed for 30 minutes, cooled to 25° C. and poured into water (500 ml). The resulting mixture is extracted with ether (3×200 ml). The organic extracts are combined, washed with brine (3×50 ml), dried over magnesium sulfate and filtered. The filtrate is evaporated in vacuo, leaving the title compound as a tan solid. The title compound is purified by recrystallization from cyclohexane.

Step B: Preparation of Methyl (E)-7-[2,4-dichloro-6-(4-fluorophenyl)phenyl]-5-hydroxy-3-oxo-6-heptenoate Methyl acetoacetate (9.56 g, 82.3 mmole) is added dropwise to a stirred suspension of sodium hydride (50% oil suspension) (3.95 g, 82.3 mmole) in anhydrous tetrahydrofuran at 0° C. under a nitrogen atmosphere. The resulting solution is stirred 15 minutes at 0° C. and then treated with a 1.6 M solution (51.5 ml, 82.3 mmole) of n-butyllithium in hexane over 5 minutes. The resulting solution is stirred 15 minutes at 0° C. and then treated with a solution of (E)-2,4-dichloro-6-(4-fluorophenyl)cinnamaldehyde (82.3 mmole) in anhydrous tetrahydrofuran (150 ml). The resulting orange solution is stirred 15 minutes at 0° C. and then quenched by dropwise addition of 12 N hydrochloric acid (ca. 20 ml). The reaction mixture is diluted with water (100 ml) and extracted with ether (3×300 ml). The organic extracts are combined, washed with brine (3×100 ml), dried over magnesium sulfate and filtered. The filtrate is evaporated in vacuo leaving the title compound as an oil.

Step C: Preparation of Methyl (E)-7-[2,4-Dichloro-6-(4-fluorophenyl)phenyl]-3,5-dihydroxy-6-heptenoate Sodium tetrahydridoborate (1.55 g, 41.1 mmole) is added with stirring to a cooled solution (5° C.) of methyl (E)-7-(2,4-dichloro-6-(4-fluorophenyl)phenyl)-5-hydroxy-3-oxo-6-heptenoate (82.3 mmole) in ethanol (200 ml) at a rate sufficient to maintain the internal temperature at 15°–20° C. The resulting solution is stirred with ice-bath cooling for 15 min. and then acidified with 6 N hydrochloric acid. The resulting mixture is diluted with water (500 ml) and extracted with ether (3×250 ml). The organic extracts are combined, washed with brine (4×100 ml), dried over magnesium sulfate and filtered. The filtrate is evaporated in vacuo, leaving the title compound as an oil.

Step D: Preparation of (E)-7-[2,4-Dichloro-6-(4-fluorophenyl)phenyl]-3,5-dihydroxy-6-heptenoic acid A solution of methyl (E)-7-[2,4-dichloro-6-(fluorophenyl)phenyl]-3,5-dihydroxy-6-heptenoate (81.8 mmole), 1 N sodium hydroxide (82 ml, 82 mmole) and ethanol (200 ml) is stirred at 25° C. for 15 min. The reaction solution is acidified with 6 N hydrochloric acid, diluted with water (400 ml) and extracted with ether (3×200 ml). The combined organic extracts are washed with brine (3×100 ml), dried over magnesium sulfate and filtered. The filtrate is evaporated in vacuo, leaving the title compound as an oil.

Step E: Preparation of (E)-trans-6-[2-(3,5-dichloro-4'-fluoro[1,1'-biphenyl]-2-yl)ethenyl]-3,4,5,6-tetrahydro-4-hydroxy-2H-pyran-2-one A solution of (E)-7-[2,4-dichlorophenyl-6-(4-fluorophenyl)phenyl]-3,5-dihydroxy-6-heptenoic acid (81.3 mmole) in toluene (300 ml) is heated at reflux in a Dean-Stark apparatus. After 2 hours the Dean-Stark apparatus is replaced with a soxhlet containing 3 A molecular sieves (100 g). The solution is refluxed for an additional 4 hours and then the toluene is removed in vacuo leaving an oil which is a mixture of cis and trans isomers of the title compound. The oil is chromatographed on a silica gel column (900 g). Elution with methylene chloride acetone (9:1, v:v; 4000 ml) provides a forerun which is discarded. Continued elution with the same eluant (500 ml) gives the trans isomer of the title compound, m.p. 121°–122° C.

Step F: Preparation and Separation of the Diastereomeric Amides (Diastereomers A and B)

A solution of (E)-trans-6-[2-(3,5-dichloro-4'-fluoro[1,1'-biphenyl]-2-yl)ethenyl]-3,4,5,6-tetrahydro-4-hydroxy-2H-pyran-2-one (68 mmole) and 1-(−)-α-methyl-benzylamine (16.5 g, 136 mmole) in tetrahydrofuran (350 ml) is refluxed for 20 hours. The tetrahydrofuran is removed in vacuo and the residue is stirred in ether (500 ml) and the precipitate collected to give diastereomer A which is twice stirred for 15 min. in refluxing ether (500 ml) to yield a colorless solid which melted at 128.5°–129° C.

Step G: Preparation of (+)-(E)-trans-6-[2-(3,5-dichloro-4'-fluoro[1,1'-biphenyl]-2-yl)ethenyl]-3,4,5,6-tetrahydro-4-hydroxy-2H-pyran-2-one Diastereomer A (1.8 mmole) of Step F is dissolved in 95% ethanol (25 ml) containing 1 N sodium hydroxide (3.6 ml, 3.6 mmole) and the solution is refluxed for 54 hours. The solvent is removed in vacuo and the residue is suspended in water (100 ml) and acidified with 6 N hydrochloric acid. This aqueous mixture is extracted with ether (3×75 ml). The ether extracts are combined, washed with brine (2×50 ml), dried over magnesium sulfate and filtered. The filtrate is evaporated in vacuo leaving the intermediate acid as an oil.

A solution of the yellow oil in toluene (150 ml) is refluxed through a soxhlet containing molecular sieves (3 A) for 5 hours. The solution is evaporated in vacuo leaving the title compound as a solid, $[\alpha]_D^{25} = +38.7°$ (C, 0.8; chloroform).

EXAMPLE 1

3,5-Dichloro-4'-fluoro-1,1'-biphenyl-2-carboxaldehyde

Step A: Preparation of
bis(μ-(acetato-0:0')bis-[3,5-dichloro-2-[(phenylimino)-methyl]phenyl-C,N]dipalladium A mixture of N-[(2,4-dichlorophenyl)-methylene]-benzene amine (2.5 g, 10 mmole) and palladium (II) acetate (2.24 g, 10 mmole) in acetic acid (50 ml) was heated at reflux for one hour with stirring. The warm turbid solution was filtered and the filtrate was diluted with water (300 ml) to give the title compound as a red solid (3.9 g, 94%). Crystallization from acetic acid-water (7:1, v:v) provided an analytical sample of the title compound, m.p. 203°–5° C.:

pmr (CDCl$_3$) δ 1.73(3H,s), 6.50(H,d,J=1.5 Hz), 6.97(2H,m), 7.12(H,d,J=7.5 Hz), 7.33(3H,m), 8.03 (H,s).

Analysis Calc. for C$_{30}$H$_{22}$Cl$_2$N$_4$O$_4$Pd$_2$ Calc.: C, 43.42; H, 2.67; N, 3.38; Found: C, 43.54; H, 2.59; N, 3.13.

Step B: Preparation of
3,5-dichloro-4'-fluoro-1,1'-biphenyl-2-carboxyaldehyde

A solution of bis(μ-(acetato-0:0')bis[3,5-dichloro-2-[(phenylimino)methyl]phenyl-C,N]dipalladium (8.29 g, 10 mmole) and triphenylphosphine (21.0 g, 80 mmole) in dry benzene (150 ml) was stirred for 30 minutes at ambient temperature under N$_2$. The 4-fluorophenyl-magnesium bromide, prepared from 4-bromofluorobenzene (15.4 g, 88 mmole) and magnesium (1.94 g, 80 mmole) in dry ether (100 ml) under N$_2$ at ambient temperature, was added to the above solution in one portion. The resultant mixture was stirred for 1 hour at ambient temperature. After the addition of 6 NHCl (50 ml) with stirring for 1 hour, the mixture was filtered. The filtrate was diluted with ether (300 ml) and washed with brine (2×100 ml). The organic layer was refiltered to remove more yellow solid and the filtrate was washed with brine (2×100 ml), dried over MgSO$_4$, filtered and evaporated. The residue was chromatographed on a silica column (1000 g). Elution with ether-hexane (1:39, v:v; 5500 ml) provided a forerun which was discarded. Continued elution with ether-hexane (1:9, v:v, 5700 ml) gave the title compound as a yellow solid (4.5 g, 84%), m.p. 73°–4° C.: pmr (CDCl$_3$) δ 7.03–7.40(5H,m), 7.53(H,d,J=1.5 Hz), 10.13(H,s).

EXAMPLE 2

Starting with bis(μ-(acetato-0:0')bis[3,5-dichloro-2[(phenylimino)methyl]phenyl-C,N]dipalladium, but substituting equal amounts of the following Grignard reagents for 4-fluorophenylmagnesium bromide in Step B of Example 1 and following the procedure of Step B there was obtained a corresponding amount of the appropriate end products listed below in Table I.

| Grignard | End Product | pmr (δ) |
| --- | --- | --- |
| 4-methylphenyl | 3,5-dichloro-4'-methyl-1,1'-biphenyl-2-carboxaldehyde | 2.40(3H,s), 7.13–7.40(5H,m) 7.50(H,d,J = 1.5Hz), 10.86(H,s) |
| 4-methoxyphenyl | 3,5-dichloro-4'-methoxy-1,1'-biphenyl-2-carboxaldehyde | 3.85(3H,s), 6.93–7.50(6H,m), 10.03(H,s) |
| 3-fluorophenyl | 3,5-dichloro-3'-fluoro-1,1'-biphenyl-2-carboxaldehyde | 6.93–7.60(6H,m), 10.16(H,s) |
| 3-methylphenyl | 3,5-dichloro-3'-methyl-1,1'-biphenyl-2-carboxaldehyde | 2.3(3H,s), 7.0–7.8(6H,m) 9.8(H,s) |
| 3,5-dimethylphenyl | 3,5-dichloro-3',5'-dimethyl-1,1'-biphenyl-2-carboxaldehyde | 2.3(6H,s), 6.9–7.5(5H,m), 10.0(H,s) |
| 4-fluoro-2-methyl phenyl | 3,5-dichloro-4'-fluoro-2'-methyl-1,1'-biphenyl-2-carboxaldehyde | 2.0(3H,s), 6.9–7.5(5H,m), 10.1(H,s) |
| 3-ethylphenyl | 3,5-dichloro-3'-ethyl-1,1'-biphenyl-2-carboxaldehyde | 1.4(3H,t), 2.9(2H,q), 7.2–7.6(6H,m), 10.0(H,s) |
| 4-fluoro-3-methyl phenyl | 3,5-dichloro-4'-fluoro-3'-methyl-1,1'-biphenyl-2-carboxaldehyde | 2.3(3H,s), 7.0–7.5(5H,m), 10.1(H,s) |
| 3,4-dichlorophenyl | 3,3',4',5-tetrachloro-1,1'-biphenyl-2-carboxaldehyde | 7.0–7.6(5H,m), 10.3(H,s) |
| 3,5-dichlorophenyl | 3,3',5,5'-tetrachloro-1,1'-biphenyl-2-carboxaldehyde | 7.1–7.6(5H,m), 10.3(H,s) |
| 2-methylphenyl | 3,5-dichloro-2'-methyl-1,1'-biphenyl-2-carboxaldehyde | 2.1(3H,s), 7–7.6(6H,m), 10.0(H,s) |
| 3-methoxyphenyl | 3,5-dichloro-3'-methoxy-1,1'-biphenyl-2-carboxaldehyde | 3.9(3H,s), 6.8–7.6(6H,m), 10.1(H,s) |

EXAMPLE 3

3,4',5-Trifluoro-1,1'-biphenyl-2-carboxaldehyde

Step A: Preparation of
N-[2,4-difluorophenyl)-methylene]benzene amine

A solution of 2,4-difluorobenzaldehyde (3.9 g, 27.4 mmole) and aniline (2.5 g, 27.4 mmole) in toluene (100 ml) was refluxed and the water was collected in a Dean-Stark apparatus. After 2 hours, the toluene was removed in vacuo to provide the title compound as a tan liquid (5.8 g, 97%) which was used in Step B without further purification: pmr (CDCl$_3$) δ6.50–7.33(7H,m), 8.00(H,m), 8.49(H,s).

Step B: Preparation of
bis(μ-(acetato-0:0')bis-[3,5-difluoro-2[(phenylimino)methyl]phenyl-C,N]dipalladium A mixture of N-[2,4-difluorophenyl)methylene]benzene amine (8.1 g, 37.3 mmole) and palladium (II) acetate (8.4 g, 37.3 mmole) in acetic acid (100 ml) was heated at reflux for 1 hour with stirring. The warm turbid solution was filtered and the filtrate was diluted with water (600 ml) to give the title compound as a yellow solid (13.4 g, 94%), m.p. dec 212°–14° C.: pmr (CDCl$_3$) δ1.80(3H,s), 6.00(H,dd,J=8 Hz, 2 Hz), δ5.0(H,td,J=8 Hz, 2 Hz), 6.90(2H,m), 7.23(3H,m), 7.92(H,s).

Step C: Preparation of 3,4′,5-trifluoro-1,1′-biphenyl-2-carboxaldehyde

A solution of bis(μ-(acetato-O:O′)bis[3,5-difluoro-2-[(phenylimino)methyl]phenyl-C,N]dipalladium (2.54 g, 3.3 mmole) and triphenylphosphine (5.24 g, 20 mmole) in dry benzene (50 ml) was stirred for 30 minutes at ambient temperature under $N_2$ and then cooled to 5° C. (ice bath). The 4-fluorophenylmagnesium bromide, prepared from 4-bromofluorobenzene (1.92 g, 11 mmole) and magnesium (0.24 g, 10 mmole) in dry ether (25 ml) under $N_2$ at ambient temperature, was added dropwise to the above solution at such a rate that the internal temperature did not exceed 10° C. After stirring the resultant mixture for one hour at 5° C., 6 N HCl (15 ml) was added and the reaction was stirred another hour at 5° C. The reaction solution was then diluted with ether (200 ml) and washed with brine (100 ml). The organic layer was filtered to remove some yellow solid which precipitated during the brine washing and the filtrate was washed with brine (2×100 ml) dried over $MgSO_4$, filtered and evaporated. The residue was chromatographed on a 60 mm chromatographic column containing 15 cm of silica gel (234–400 mesh). Elution with methylene chloride-hexane (1:1; v:v; 960 ml) provided a forerun which was discarded. Continued elution (940 ml) gave the title compound as a white solid (1.2 g, 76%), m.p. 69°–71° C.: pmr (CDCl$_3$) δ 6.82–7.10(2H,m), 7.16–7.47(4H,m), 10.0(H,s).

Analysis Calc. for $C_{13}H_7F_3O$ Calc.: C, 66.10; H, 2.99; Found: C, 65.86; H, 2.70.

EXAMPLE 4

5-Chloro-4′-fluoro-3,3′-dimethyl-1,1′-biphenyl-2-carboxaldehyde

Step A: Preparation of N-[(4-chloro-2-methylphenyl)-methylene]benzeneamine

A mixture of 4-chloro-2-methylbenzaldehyde (3.5 g, 22.6 mmol) and aniline (2.11 g, 22.6 mmol) in toluene (40 ml) was heated at reflux in a Dean-Stark apparatus for 1 hour. The mixture was cooled and evaporated in vacuo to leave an oily residue. The residue was redissolved in ether and washed with 5% sodium bicarbonate solution. The organic phase was separated, dried over $MgSO_4$ and filtered. The filtrate was concentrated in vacuo to afford an oily residue which was purified by distillation via a Kugelrohr apparatus (oven temperature 160° C., 0.5 mm) to provide the title compound (4.0 g, 17.4 mmol, 77%) as a viscous oil; pmr (CDCl$_3$) δ 2.5(3H,s), 6.3–7.5(7H,m), 7.95(H,d), 8.6(H,s).

Step B: Preparation of 5-Chloro-4′-fluoro-3,3′-dimethyl-1,1′-biphenyl-2-carboxaldehyde By substituting an equimolar amount of N-[(4-chloro-2-methylphenyl)methylene]benzeneamine in place of N-[(2,4-dichlorophenyl)methylene]benzeneamine in Step A of Example 1 and replacing the 4-fluorophenylmagnesium bromide with an equimolar amount of 4-fluoro-3-methylphenylmagnesium bromide in Step B of Example 1 and following the procedures described therein, there was obtained a corresponding amount of the title compound; pmr (CDCl$_3$) δ 2.30(3H,d), 2.60(3H,s), 7.1–7.3(5H,m), 9.9(H,s).

EXAMPLE 5

3′,4′-Dichloro-3,5-dimethyl-1,1′-biphenyl-2-carboxaldehyde

By substituting an equimolar amount of N-[(2,4-dimethylphenyl)methylene]benzeneamine in place of N-[(2,4-dichlorophenyl)methylene]benzeneamine in Step A of Example 1 and replacing the 4-fluorophenylmagnesium bromide with an equimolar amount of 3,4-dichlorophenylmagnesium bromide in Step B of Example 1 and following the procedures described therein, there was obtained a corresponding amount of the title compound, m.p. 80°–81° C.; pmr (CDCl$_3$) δ 2.4(3H,s), 2.6(3H,s), 7.0–7.5(5H,m), 10.0(H,s).

Analysis calc. for $C_{15}H_{12}Cl_2O$: C, 64.54; H, 4.33; Found: C, 64.83; H, 4.45.

EXAMPLE 6

Employing the procedure substantially as described in Example 5, but substituting for the 3,4-dichlorophenylmagnesium bromide used therein, an equimolecular amount of the Grignard reagents listed in Table II there were prepared the substituted biphenyl-2-carboxaldehydes, also listed in Table II.

| Grignard | Product | pmr (δ) |
| --- | --- | --- |
| 4-Fluoro-3-methylphenyl | 4′-fluoro-3,3′,5-trimethyl-1,1′-biphenyl-2-carboxaldehyde | 2.4(3H,d), 2.5(3H,s), 2.7(3H,s), 7.0–7.3(5H,m), 9.9(H,s) |
| 3,5-dimethylphenyl | 3,3′,5,5′-tetramethyl-1,1′-biphenyl-2-carboxaldehyde | 2.3(9H,m), 2.6(3H,s) 6.8–7.0(5H,m), 10.0(H,s) |
| 4-fluorophenyl | 4′-fluoro-3,5-dimethyl-1,1′-biphenyl-2-carboxaldehyde | 2.4(3H,s), 2.6(3H,s) 7.0–7.4(6H,m), 10.0(H,s) |

EXAMPLE 7

3′,4′-Dichloro-3,6-dimethyl-1,1′-biphenyl-2-carboxaldehyde

By substituting an equimolar amount of N-[(2,5-dimethylphenyl)methylene]benzeneamine in place of N-[(2,4-dichlorophenyl)methylene]benzeneamine in Step A of Example 1 and replacing the 4-fluorophenylmagnesium bromide with an equimolar amount of 3,4-dichlorophenylmagnesium bromide in Step B of Example 1 and following the procedures described therein, there was obtained a corresponding amount of the title compound as a pale yellow gum; pmr (CDCl$_3$) δ 2.0(3H,s), 2.6(3H,s), 7.0–7.6(5 H,m), 9.9(H,s).

EXAMPLE 8

3-Chloro-4′-fluoro-3′-methyl-1,1′-biphenyl-2-carboxaldehyde

Step A: Preparation of N-[(2-chlorophenyl)methylene]-benzeneamine

When the procedure of Example 3, Step A, is followed, except that an equimolar quantity of 2-chlorobenzaldehyde is used in place of 2,4-difluorobenzaldehyde, there is obtained the title compound as a viscous oil.

Anal. Calc'd for $C_{13}H_{10}ClN$:
%C, 72.40; %H, 4.67; %N, 6.49; Found: %C, 72.35; %H, 5.02; %N, 6.46.

Step B: Preparation of 3-chloro-4′-fluoro-3′-methyl-1,1′-biphenyl-2-carboxaldehyde By substituting an equimolar quantity of N-[(2-chlorophenyl)methylene]benzeneamine in place of N-[(2,4-dichlorophenyl)methylene]benzeneamine in Step A of Example 1 and replacing the 4-fluorophenylmagnesium bromide with an equimolar amount of 4-fluoro-3-methylphenylmagnesium bromide in Step B of Example 1 and following the procedures described therein, there is obtained the title compound, m.p. 74°–79° C.

Anal. Calc'd for $C_{14}H_{10}ClFO$: %C, 67.62; %H, 4.05. Found: %C, 67.83; %H, 4.09.

What is claimed is:
1. A compound selected from:
3,5-dichloro-4′-fluoro-1,1′-biphenyl-2-carboxaldehyde;
3,5-dimethyl-4′-fluoro-1,1′-biphenyl-2-carboxaldehyde;
3,3′,5-trimethyl-4′-fluoro-1,1′-biphenyl-2-carboxaldehyde; or
3,3′,5,5′-tetramethyl-1,1′-biphenyl-2-carboxaldehyde.

* * * * *